United States Patent
Wu et al.

(10) Patent No.: US 10,097,390 B1
(45) Date of Patent: Oct. 9, 2018

(54) IMPLANTABLE WIRELESS DEVICE FOR TRANSMITTING DATA

(71) Applicant: NATIONAL CHIAO TUNG UNIVERSITY, Hsinchu (TW)

(72) Inventors: Chung-Yu Wu, Hsinchu (TW); Cheng-Hsiang Cheng, New Taipei (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 15/954,987

(22) Filed: Apr. 17, 2018

(30) Foreign Application Priority Data

Feb. 8, 2018 (TW) .............................. 107104490 A (51) Int. Cl.
| | | |
|---|---|---|
| *H04L 27/00* | (2006.01) | |
| *H04L 27/20* | (2006.01) | |
| *H04L 27/227* | (2006.01) | |
| *H04B 1/04* | (2006.01) | |
| *H04B 5/00* | (2006.01) | |

(Continued)

(52) U.S. Cl.
CPC .......... *H04L 27/2035* (2013.01); *A61B 5/076* (2013.01); *H03L 7/0807* (2013.01); *H03L 7/0895* (2013.01); *H03L 7/0995* (2013.01); *H04B 1/04* (2013.01); *H04B 5/0031* (2013.01);

(Continued)

(58) Field of Classification Search
CPC .......... H04W 56/00; H04L 2027/0016; H04L 2027/0057; H04L 27/2273; G06K 19/0723

USPC ....... 375/327, 324; 455/41.2, 502, 258, 259, 455/260, 39, 41.1; 329/325, 304
See application file for complete search history.

(56) References Cited

U.S. PATENT DOCUMENTS

| | | | | |
|---|---|---|---|---|
| 4,105,975 A | * | 8/1978 | Sanders | .............. H04L 27/2273 375/327 |
| 8,159,288 B2 | | 4/2012 | Luo et al. | |

(Continued)

OTHER PUBLICATIONS

Cheng-Hsiang Cheng, Ping-Yuan Tsai, Tzu-Yi Yang, Wan-Hsueh Cheng, Ting-Yang Yen, Zhicong Luo, Xin-Hong Qian, Zhi-Xin Chen, Tsu-Han Lin, Wei-Hong Cheng, Wei-Ming Chen, Sheng-Fu Liang, Fu-Zen Shaw, Cheng-Siu Chang, Fu-Yuan Shih, Yue-Loong Hsin, Chen-Yi Lee, Ming-Dou Ker, Chung-Yu Wu; A Fully Integrated Closed-Loop Neuromodulation SoC with Wireless Power and Bi-directional Data Telelmetry for Real-Time Human Epileptic Seizure Control; 2017 Symposium on VLSI Circuits Digest of Technical, 2017, pp. C44-C45.

*Primary Examiner* — Leila Malek
(74) *Attorney, Agent, or Firm* — Rosenberg, Klein & Lee (57) ABSTRACT

An implantable wireless device for transmitting data includes an external control device and an internal processing device. The external control device receives digital data and an alternating current carrier signal and uses the alternating current carrier signal to modulate the digital data into a phase shift keying modulation signal. The digital data have a plurality of time points that binary data change. The internal processing device includes a phase-lock loop (PLL)-based phase shift keying demodulator. The PLL-based phase shift keying demodulator obtains a ripple voltage signal according to the phase shift keying modulation signal. The ripple voltage signal decreases from a fixed voltage value at each of the plurality of time points and then increases to the (Continued)

fixed voltage value. The PLL-based phase shift keying demodulator demodulates the ripple voltage signal into the digital data.

10 Claims, 5 Drawing Sheets

(51) Int. Cl.
*A61B 5/07* (2006.01)
*H03L 7/08* (2006.01)
*H03L 7/089* (2006.01)
*H03L 7/099* (2006.01)

(52) U.S. Cl.
CPC ....... *H04B 5/0081* (2013.01); *H04L 27/2272* (2013.01)

(56) References Cited

U.S. PATENT DOCUMENTS

| | | | |
|---|---|---|---|
| 2003/0227990 A1* | 12/2003 | Hsu | H03L 7/0891 375/376 |
| 2007/0058753 A1 | 3/2007 | Saavedra et al. | |
| 2010/0277234 A1* | 11/2010 | Luo | A61N 1/3727 329/307 |
| 2011/0081872 A1* | 4/2011 | Bar-Sade | H04L 12/46 455/77 |

\* cited by examiner

IMPLANTABLE WIRELESS DEVICE FOR TRANSMITTING DATA

This application claims priority for Taiwan patent application no. 107104490 filed on Feb. 8, 2018, the content of which is incorporated by reference in its entirety.

BACKGROUND OF THE INVENTION

Field of the Invention

The present invention relates to a wireless device for transmitting data, particularly to an implantable wireless device for transmitting data, which retrieves digital data when binary data change.

Description of the Related Art

With the development of integrated circuits (ICs) and the medical improvement, people have a better understanding of various psychological signals and fabricate micro-electronic medical components. In the past, the systems for detecting neuro-physiological signals are heavy and time-consuming. Presently, portable or implantable devices are used to inspect health of people anywhere and anytime. In the implantable medical devices, the wireless charging and data transmitting system plays a very important role. In order to extend the using time of the implantable biomaterials to avoid taking risks in a surgical operation, the wireless charging technology is necessary for the implantable biomaterials. Besides, since doctors and patients need to observe relative parameters of the implantable biomaterials anytime, the wireless data transmitting system is used as a communication medium between the implantable biomaterials and the outside.

Figure 1:
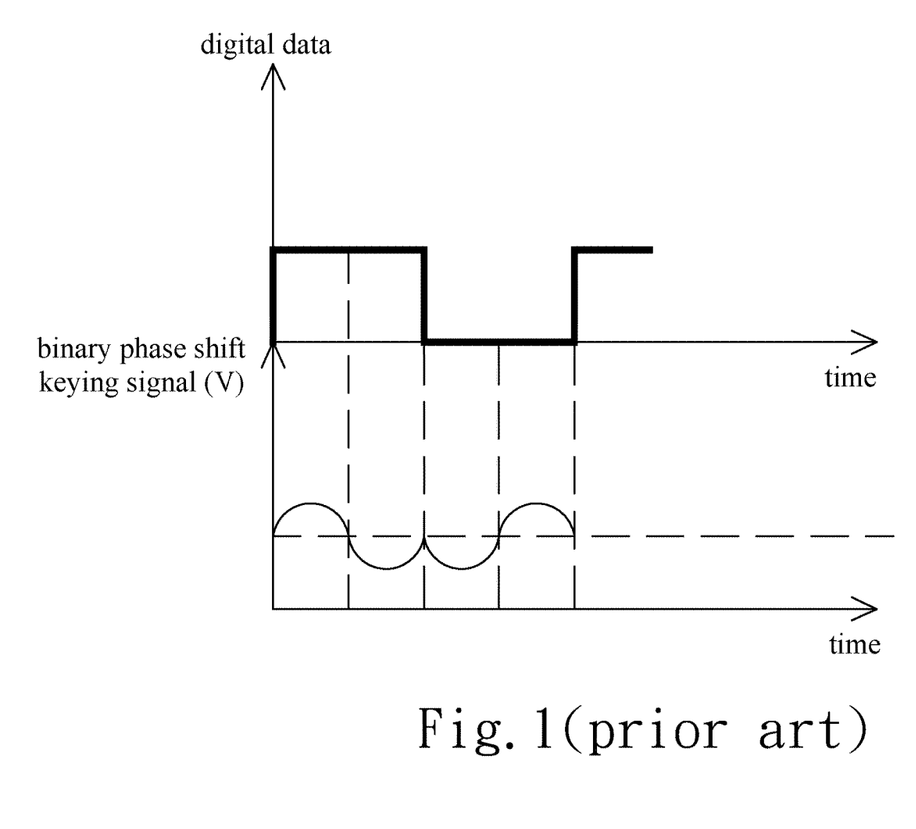
FIG. 1 is a diagram showing waveforms of digital data and a binary phase shift keying modulation signal with a complete period in the conventional technology.
Figure 2:
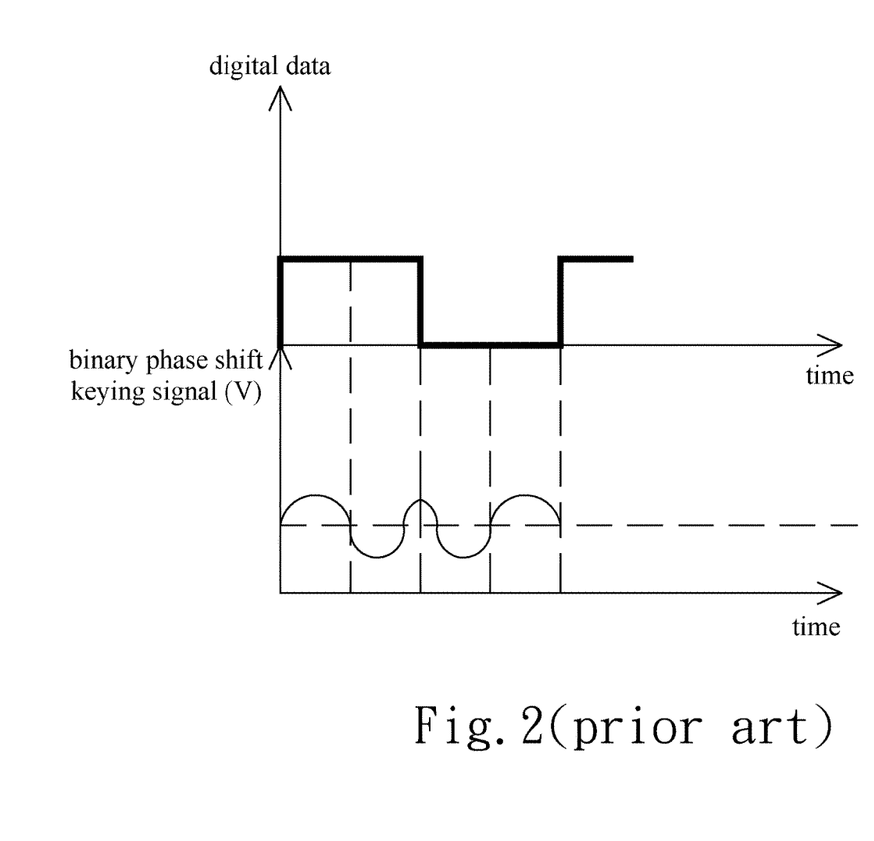
FIG. 2 is a diagram showing waveforms of digital data and a binary phase shift keying modulation signal with an incomplete period in the conventional technology.

In the existing technology, the binary phase shift keying (BPSK) demodulator is only applied to the transmission channel with low quality factor and high bandwidth. Thus, the BPSK signal can be rapidly transformed. However, in the bioelectrical industry, many implantable biochips are wirelessly driven by electricity. In order to reduce the area of the implantable device, the wireless charging circuit and the wireless data transmitting circuit share one coil. Besides, considering the efficiency of wireless charging, using a coil with high quality factor and low bandwidth is necessary. Refer to FIG. 1. If the digital data "0" or "1" corresponds to a binary phase shift keying signal with a complete period, the boundary of the digital data will be demodulated. The boundary of the digital data represents the variation of the digital data. Then, refer to FIG. 2. If the digital data "0" or "1" corresponds to a binary phase shift keying signal with an incomplete period, the boundary of the digital data will be not demodulated. This is because low bandwidth needs more time to change a phase of the signal.

To overcome the abovementioned problems, the present invention provides an implantable wireless device for transmitting data, so as to solve the afore-mentioned problems of the prior art.

SUMMARY OF THE INVENTION

The primary objective of the present invention is to provide an implantable wireless device for transmitting data, which uses a phase-lock loop (PLL)-based phase shift keying demodulator to precisely and rapidly to obtain digital data when binary data change.

To achieve the abovementioned objectives, the present invention provides an implantable wireless device for transmitting data, which comprises an external control device and an internal processing device implanted in a physiological tissue. The external control device comprises a phase shift keying (PSK) modulator and a first wireless transmission coil. The PSK modulator receives digital data and an alternating current (AC) carrier signal and uses the AC carrier signal to modulate the digital data into a phase shift keying (PSK) modulation signal, and the digital data have a plurality of time points that binary data change. The quality factor of the first wireless transmission coil is larger than 100, and the first wireless transmission coil is electrically connected to the phase shift keying modulator. The internal processing device comprises a second wireless transmission coil, a phase-lock loop (PLL)-based phase shift keying demodulator, and an alternating current (AC) to direct current (DC) converter. The quality factor of the second wireless transmission coil is larger than 100. The PLL-based phase shift keying demodulator is electrically connected to the second wireless transmission coil, receives the phase shift keying modulation signal through the first wireless transmission coil and the second wireless transmission coil, and obtains a ripple voltage signal according to the phase shift keying modulation signal. The ripple voltage signal decreases from a fixed voltage value at each of the plurality of time points and then increases to the fixed voltage value. The phase-lock loop-based phase shift keying demodulator demodulates the ripple voltage signal into the digital data. For example, the phase shift keying modulator is a binary phase shift keying (BPSK) modulator, the phase shift keying modulation signal is a binary phase shift keying modulation signal, and the phase-lock loop-based phase shift keying demodulator is a phase-lock loop-based binary phase shift keying demodulator. The AC to DC converter is electrically connected to the second wireless transmission coil, receives the phase shift keying modulation signal through the first wireless transmission coil and the second wireless transmission coil, and converts the phase shift keying modulation signal into a supplying direct current voltage. The supplying direct current voltage is used to provide electricity.

In an embodiment of the present invention, the phase-lock loop-based phase shift keying demodulator further comprises a phase-lock loop, a triggering detector, and a logic assembly. For example, the logic assembly is a DQ flip-flop. The phase-lock loop is electrically connected to the second wireless transmission coil, receives the phase shift keying modulation signal through the first wireless transmission coil and the second wireless transmission coil, and obtains the ripple voltage signal according to the phase shift keying modulation signal. The triggering detector is electrically connected to the phase-lock loop and receives the ripple voltage signal, and generates a positive pulse signal at each of the plurality of time points. The logic assembly is electrically connected to the triggering detector to receive the positive pulse signal, thereby generating the digital data.

In an embodiment of the present invention, the triggering detector further comprises a low pass filter, a comparator, and a Schmitt trigger. The low pass filter is electrically connected to the phase-lock loop and receives the ripple voltage signal to generate a filtering signal. The comparator has a positive input terminal, a negative input terminal, and an output terminal. The negative input terminal of the comparator is electrically connected to the phase-lock loop and the low pass filter. The low pass filter is electrically connected between the positive input terminal and the negative input terminal of the comparator. The positive input terminal and the negative input terminal of the comparator respectively receive the filtering signal and the ripple voltage signal. The comparator compares the filtering signal with the ripple voltage signal and uses the output terminal to generate a comparison signal. The Schmitt trigger is electrically connected to the output terminal of the comparator and the logic assembly to receive the comparison signal and generate the positive pulse signal at each of the plurality of time points according to the comparison signal.

In an embodiment of the present invention, the phase-lock loop-based phase shift keying demodulator further comprises a clock recovery circuit electrically connected to the second wireless transmission coil and the triggering detector, receiving the positive pulse signal and the phase shift keying modulation signal, and dividing a frequency of the phase shift keying modulation signal by a given value to generate a clock signal. The frequency of the clock signal corresponds to the data rate of the digital rate. When the clock recovery circuit receives the positive pulse signal, the clock recovery circuit resets the clock signal. For example, the period of the clock signal is A seconds, the data rate is B bits per second, A is a positive number, B is a natural number, and A×B=1.

In an embodiment of the present invention, the internal processing device further comprises a processor electrically connected to the logic assembly and the clock recovery circuit and receiving the clock signal and the digital data. When the clock signal rises from a negative level to a positive level, the processor correctly retrieves the digital data.

In an embodiment of the present invention, the phase-lock loop further comprises a phase frequency detector, a charge pump circuit, a loop filter, a voltage controlled oscillator, and a frequency divider. The phase frequency detector is electrically connected to the second wireless transmission coil, receives the phase shift keying modulation signal through the first wireless transmission coil and the second wireless transmission coil, receives an alternating current feedback signal, and uses the alternating current feedback signal and the phase shift keying modulation signal to generate a first digital value and a second digital value. The charge pump circuit is electrically connected to the phase frequency detector and receives the first digital value and the second digital value. The loop filter is electrically connected to the charge pump circuit and the triggering detector. The charge pump circuit uses a current source to charge or discharge the loop filter according to the first digital value and the second digital value, so as to transmit a current signal to the loop filter, and the loop filter converts the current signal into the ripple voltage signal. The voltage controlled oscillator is electrically connected to the loop filter and receives the ripple voltage signal to generate an alternating current oscillating signal. The frequency divider is electrically connected to the voltage controlled oscillator and the phase frequency detector, receives the alternating current oscillating signal, and divides a frequency of the alternating current oscillating signal by a fixed value to generate the alternating current feedback signal.

In an embodiment of the present invention, the voltage controlled oscillator further comprises a first current mirror, a first N-channel metal oxide semiconductor field effect transistor (NMOSFET), a second N-channel metal oxide semiconductor field effect transistor (NMOSFET), a third N-channel metal oxide semiconductor field effect transistor (NMOSFET), a controller, a second current mirror, and a ring oscillator. The first current mirror generates a first current. The drain of the first NMOSFET is electrically connected to the first mirror and the gate of the first NMOSFET is electrically connected to the loop filter and the triggering detector to receive the ripple voltage signal. The drain of the second NMOSFET is electrically connected to the source of the first NMOSFET, and the gate of the second NMOSFET is electrically connected to the drain of the first NMOSFET, and the source of the second NMOSFET is grounded. The first NMOSFET and the second NMOSFET uses the ripple voltage signal to receive the first current, thereby establishing a node voltage at the source of the first NMOSFET. The source of the third NMOSFET is electrically connected to the source of the first NMOSFET and the drain of the second NMOSFET to receive the node voltage, and the gate of the third NMOSFET receives a high level voltage. The controller is electrically connected to the drain of the third NMOSFET, receives an external voltage, and uses the external voltage to turn on the third NMOSFET and generate a start voltage. The second current mirror is electrically connected to the controller and receives the start voltage to generate a second current. The ring oscillator is electrically connected to the second current mirror and the frequency divider and receives the second current to generate the alternating current oscillating signal. Since the sources of the first NMOSFET and the third NMOSFET are electrically connected to each other, process variations have a reduced influence on the frequency of the alternating current oscillating signal. Besides, considering area and power, the ring oscillator is a better choice.

Below, the embodiments are described in detail in cooperation with the drawings to make easily understood the technical contents, characteristics and accomplishments of the present invention.

DETAILED DESCRIPTION OF THE INVENTION

Reference will now be made in detail to embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, methods and apparatus in accordance with the present disclosure. It is to be understood that elements not specifically shown or described may take various forms well known to those skilled in the art. Many alternatives and modifications will be apparent to those skilled in the art, once informed by the present disclosure.

Figure 3:
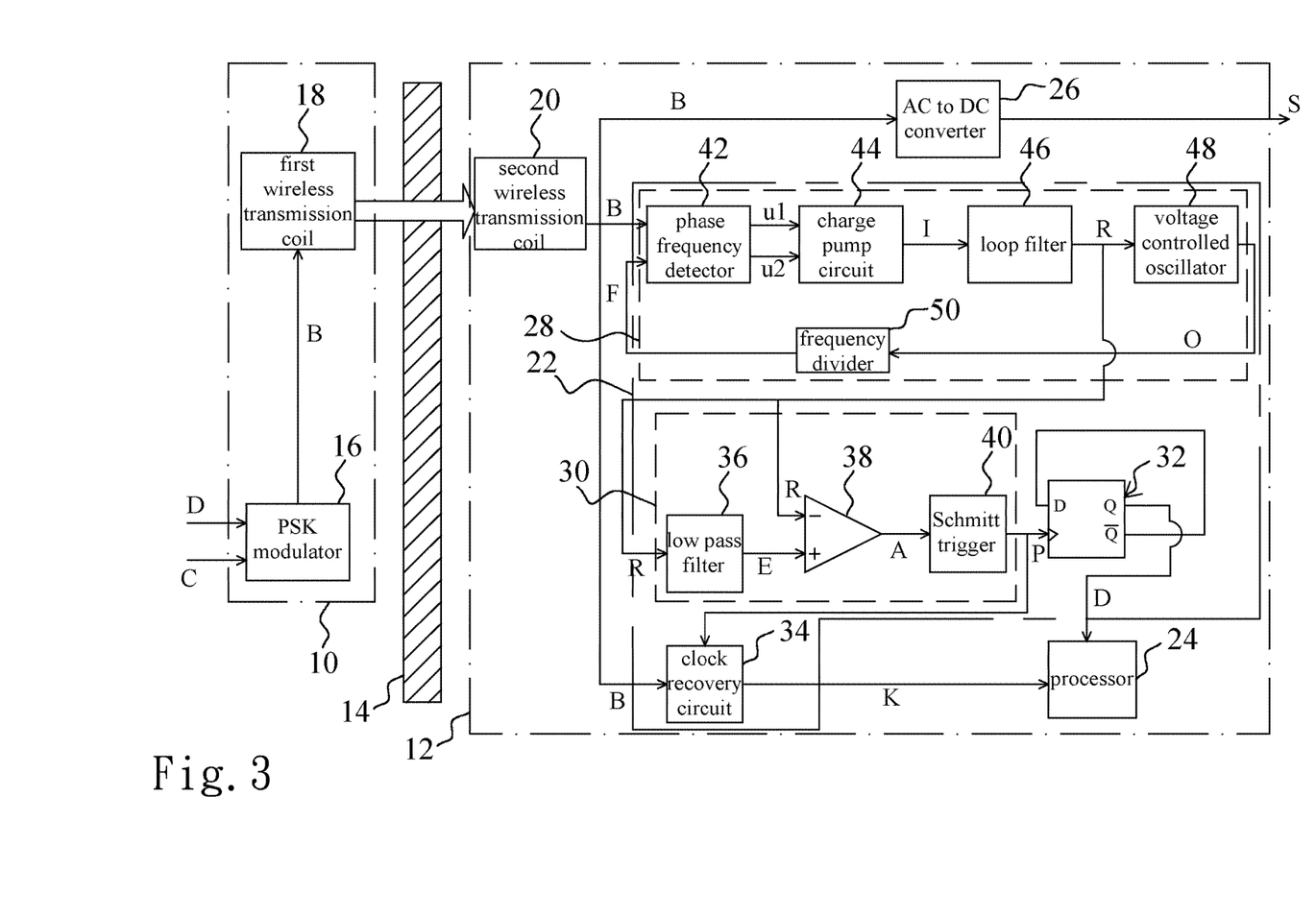
FIG. 3 is a block diagram showing a circuit of an implantable wireless device for transmitting data according to an embodiment of the present invention.
Figure 4:
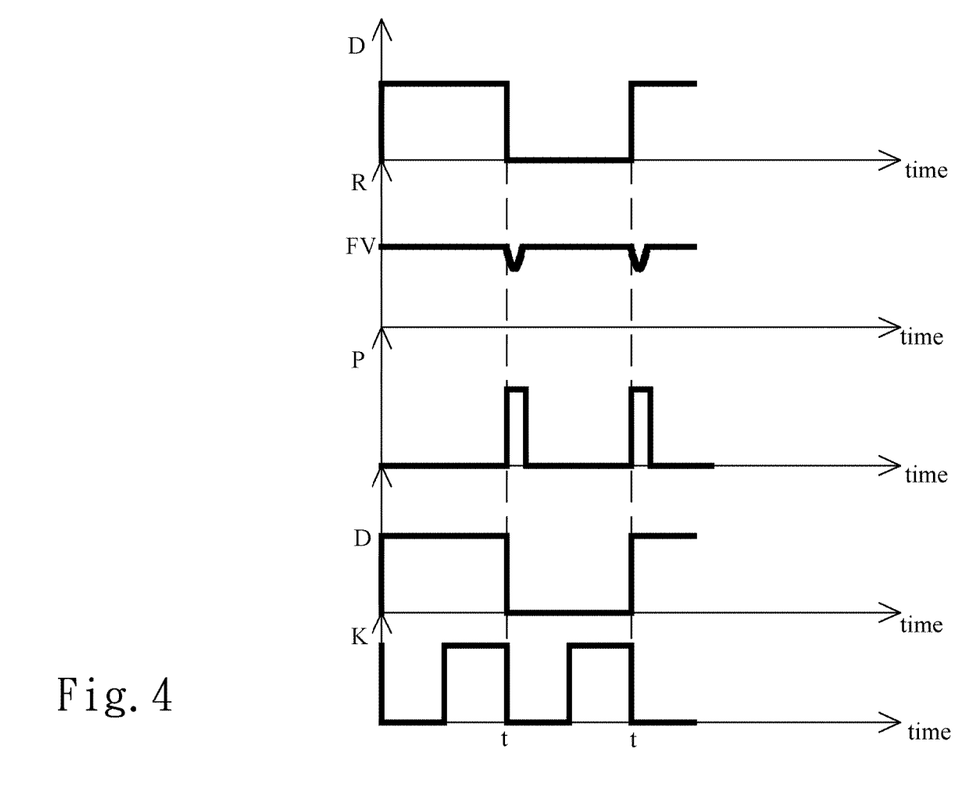
FIG. 4 is a diagram showing waveforms of digital data, a ripple voltage signal, a positive pulse signal, and a clock signal according to an embodiment of the present invention.

Refer to FIG. 3 and FIG. 4. The implantable wireless device for transmitting data is introduced as follows. Each of digital data D, a ripple voltage signal R, a positive pulse signal P, and a clock signal K shown in FIG. 4 has a unit of a voltage. The implantable wireless device for transmitting data comprises an external control device 10 and an internal processing device 12 implanted in a physiological tissue 14. The external control device 10 comprises a phase shift keying (PSK) modulator 16 and a first wireless transmission coil 18. The quality factor of the first wireless transmission coil is larger than 100. The PSK modulator 16 receives digital data D and an alternating current (AC) carrier signal C and uses the AC carrier signal C to modulate the digital data D into a phase shift keying (PSK) modulation signal B. The digital data D have a plurality of time points t that binary data change. The first wireless transmission coil 18 is electrically connected to the phase shift keying modulator 16. The internal processing device 12 comprises a second wireless transmission coil 20, a phase-lock loop (PLL)-based phase shift keying demodulator 22, a processor 24 and an alternating current (AC) to direct current (DC) converter 26. The quality factor of the second wireless transmission coil 20 is larger than 100. The PLL-based phase shift keying demodulator 22 is electrically connected to the second wireless transmission coil 20, receives the phase shift keying modulation signal B through the first wireless transmission coil 18 and the second wireless transmission coil 20, and obtains a ripple voltage signal R according to the phase shift keying modulation signal B. The ripple voltage signal R decreases from a fixed voltage value FV at each of the plurality of time points t and then increases to the fixed voltage value FV. The phase-lock loop-based phase shift keying demodulator 22 demodulates the ripple voltage signal R into the digital data D. In the embodiment, the phase shift keying modulator 16 is a binary phase shift keying (BPSK) modulator, the phase shift keying modulation signal B is a binary phase shift keying modulation signal, and the phase-lock loop-based phase shift keying demodulator 22 is a phase-lock loop-based binary phase shift keying demodulator. Besides, the AC to DC converter 26 is electrically connected to the second wireless transmission coil 20, receives the phase shift keying modulation signal B through the first wireless transmission coil 18 and the second wireless transmission coil 20, and converts the phase shift keying modulation signal B into a supplying direct current voltage S. The supplying direct current voltage S is used to provide electricity for biomedical components.

The phase-lock loop-based phase shift keying demodulator 22 further comprises a phase-lock loop 28, a triggering detector 30, a logic assembly 32, and a clock recovery circuit 34. For example, the logic assembly 32 is a DQ flip-flop. The phase-lock loop 28 is electrically connected to the second wireless transmission coil 20, receives the phase shift keying modulation signal B through the first wireless transmission coil 18 and the second wireless transmission coil 20, and obtains the ripple voltage signal T according to the phase shift keying modulation signal B. The triggering detector 30 is electrically connected to the phase-lock loop 28 and receives the ripple voltage signal R, and generates a positive pulse signal P at each of the plurality of time points t. The logic assembly 32 is electrically connected to the triggering detector 30 to receive the positive pulse signal P, thereby generating the digital data D. The clock recovery circuit 34 is electrically connected to the second wireless transmission coil 20 and the triggering detector 30, receives the positive pulse signal P and the phase shift keying modulation signal B, and divides the frequency of the phase shift keying modulation signal B by a given value to generate a clock signal K. The given value is $2^n$. n is a natural number. For example, the frequency of the phase shift keying modulation signal B and the AC carrier signal C is 13.56 MHz, the frequency of the clock signal K is 211 kHz, and the given value is $2^6$. The frequency of the clock signal corresponds to the data rate of the digital rate. For example, the period of the clock signal K is A seconds, the data rate is B bits per second. A binary datum of the digital data D occupies one bit. A is a positive number, B is a natural number, and A×B=1. Specifically, A equals to 1/(211 k), and B equals to 211. When the clock recovery circuit 34 receives the positive pulse signal P, the clock recovery circuit 34 resets the clock signal K. When the clock recovery circuit 34 resets the clock signal K, the clock signal K immediately descends to a negative level.

The triggering detector 30 further comprises a low pass filter 36, a comparator 38, and a Schmitt trigger 40. The low pass filter 36 is electrically connected to the phase-lock loop 28 and receives the ripple voltage signal R to generate a filtering signal E. Compared with the ripple voltage signal R, the filtering signal E has lower variations. The comparator 38 has a positive input terminal, a negative input terminal, and an output terminal. The negative input terminal of the comparator 38 is electrically connected to the phase-lock loop 28 and the low pass filter 36. The low pass filter 36 is electrically connected between the positive input terminal and the negative input terminal of the comparator 38. The positive input terminal and the negative input terminal of the comparator 38 respectively receive the filtering signal E and the ripple voltage signal R. The comparator compares the filtering signal E with the ripple voltage signal R and uses the output terminal to generate a comparison signal A. The Schmitt trigger 40 is electrically connected to the clock recovery circuit 34, the output terminal of the comparator 38 and the logic assembly 32 to receive the comparison signal A and generate the positive pulse signal P at each of the plurality of time points t that the binary data change according to the comparison signal A.

The processor 24 is electrically connected to the logic assembly 32 and the clock recovery circuit 34 and receives the clock signal K and the digital data D. When the clock recovery circuit 34 receives the positive pulse signal P, the clock recovery circuit 34 resets the clock signal K. Besides, A×B=1. Thus, when the clock signal K rises from the negative level to a positive level, the processor 24 correctly retrieves the digital data D.

The phase-lock loop 28 further comprises a phase frequency detector 42, a charge pump circuit 44, a loop filter 46, a voltage controlled oscillator 48, and a frequency divider 50. The phase frequency detector 42 is electrically connected to the second wireless transmission coil 20, receives the phase shift keying modulation signal B through the first wireless transmission coil 18 and the second wireless transmission coil 20, receives an alternating current feedback signal F, and uses the alternating current feedback signal F and the phase shift keying modulation signal B to generate a first digital value u1 and a second digital value u2. The charge pump circuit 44 is electrically connected to the phase frequency detector 42 and receives the first digital value u1 and the second digital value u2. The loop filter 46 is electrically connected to the charge pump circuit 44 and the low pass filter 36 and the negative input terminal of the comparator 38 of the triggering detector 30. The charge pump circuit 44 uses a current source to charge or discharge the loop filter 46 according to the first digital value u1 and the second digital value u2, so as to transmit a current signal I to the loop filter 46, and the loop filter 46 converts the current signal I into the ripple voltage signal R. The voltage controlled oscillator 48 is electrically connected to the loop filter 46 and receives the ripple voltage signal R to generate an alternating current oscillating signal O. The frequency divider 50 is electrically connected to the voltage controlled oscillator 48 and the phase frequency detector 42, receives the alternating current oscillating signal O, and divides the frequency of the alternating current oscillating signal O by a fixed value to generate the alternating current feedback signal F. The fixed value is a positive number, such as 128. Since the phase-lock loop 28 can synchronizes the phase and frequency of the phase shift keying modulation signal B and the alternating current feedback signal F, the ripple voltage signal R is obtained and provided to the triggering detector 30 and the logic assembly 32 for precisely and rapidly demodulating the digital data D that the binary data change.

The operation of the implantable wireless device for transmitting data of the present invention is described as follows. Firstly, the PSK modulator 16 receives digital data D and an AC carrier signal C and uses the AC carrier signal C to modulate the digital data D into a PSK modulation signal B. The digital data D have a plurality of time points t that binary data change. Then, the PSK modulation signal B is transmitted to the phase frequency detector 42, the AC to DC converter 26, and the clock recovery circuit 34 through the first wireless transmission coil 18 and the second wireless transmission coil 20. The AC to DC converter 26 converts the PSK modulation signal B into a supplying direct current voltage S to supply electricity.

The phase frequency detector 42 receives an alternating current feedback signal F, and uses the alternating current feedback signal F and the PSK modulation signal B to generate a first digital value u1 and a second digital value u2. The charge pump circuit 44 receives the first digital value u1 and the second digital value u2 and uses a current source to charge or discharge the loop filter 46 according to the first digital value u1 and the second digital value u2, so as to transmit a current signal I to the loop filter 46. The loop filter 46 converts the current signal I into the ripple voltage signal R. The voltage controlled oscillator 48 receives the ripple voltage signal R to generate an alternating current oscillating signal O. The frequency divider 50 receives the alternating current oscillating signal O, and divides the frequency of the alternating current oscillating signal O by a fixed value to generate the alternating current feedback signal F.

The ripple voltage signal R is transmitted to the low pass filter 36 and the comparator 38. The low pass filter 36 filters out the ripple voltage signal R to generate a filtering signal E. The comparator 38 receives the filtering signal E and compares the filtering signal E with the ripple voltage signal R to generate a comparison signal A. The Schmitt trigger 40 receives the comparison signal A and generates the positive pulse signal P at each of the plurality of time points t that the binary data change according to the comparison signal A. The positive pulse signal P is transmitted to the logic assembly 32 and the clock recovery circuit 34. The logic assembly 32 uses the positive pulse signal P to generate the digital data D. The clock recovery circuit 34 divides the frequency of the PSK modulation signal B by a given value to generate a clock signal K. When the clock recovery circuit 34 receives the positive pulse signal P, the clock recovery circuit 34 resets the clock signal K. Finally, when the clock signal K rises from a negative level to a positive level, the processor 24 correctly retrieves the digital data D.

Figure 5:
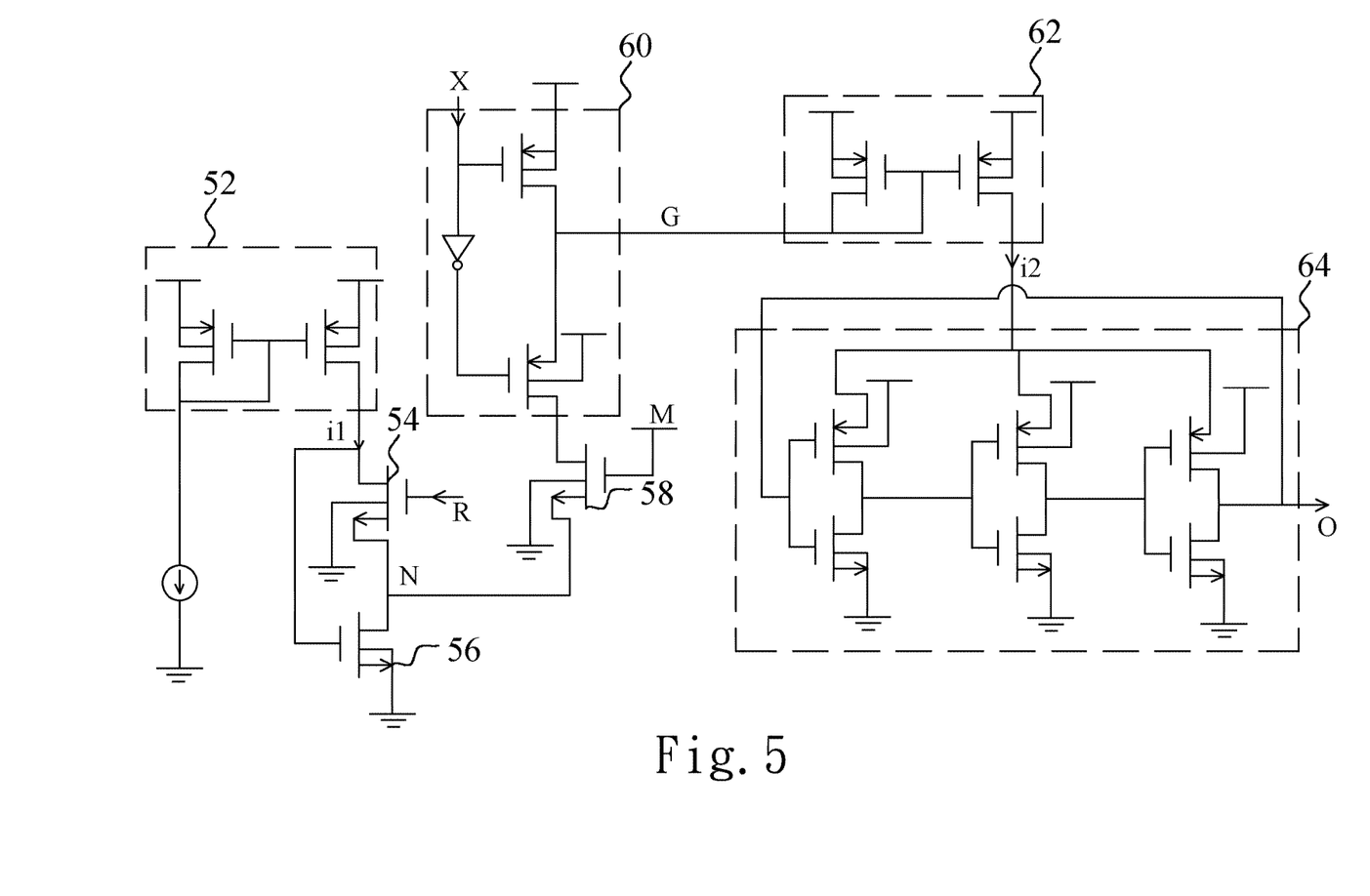
FIG. 5 is a diagram showing a circuit of a voltage controlled oscillator according to an embodiment of the present invention.

Refer to FIG. 3 and FIG. 5. The voltage controlled oscillator 48 further comprises a first current mirror 52, a first N-channel metal oxide semiconductor field effect transistor (NMOSFET) 54, a second N-channel metal oxide semiconductor field effect transistor (NMOSFET) 56, a third N-channel metal oxide semiconductor field effect transistor (NMOSFET) 58, a controller 60, a second current mirror 62, and a ring oscillator 64. The first current mirror 52 generates a first current i1. The drain of the first NMOSFET 54 is electrically connected to the first mirror 52 and the gate of the first NMOSFET 54 is electrically connected to the loop filter 46 and the low pass filter 36 and the comparator 38 of the triggering detector 30 to receive the ripple voltage signal R. The drain of the second NMOSFET 56 is electrically connected to the source of the first NMOSFET 54, and the gate of the second NMOSFET 56 is electrically connected to the drain of the first NMOSFET 54, and the source of the second NMOSFET 56 is grounded. The first NMOSFET 54 and the second NMOSFET 56 uses the ripple voltage signal R to receive the first current i1, thereby establishing a node voltage N at the source of the first NMOSFET 54. The source of the third NMOSFET 58 is electrically connected to the source of the first NMOSFET 54 and the drain of the second NMOSFET 56 to receive the node voltage N, and the gate of the third NMOSFET 58 receives a high level voltage M. The controller 60 is electrically connected to the drain of the third NMOSFET 58, receives an external voltage X, and uses the external voltage X to turn on the third NMOSFET 58 and generate a start voltage G. The second current mirror 62 is electrically connected to the controller 60 and receives the start voltage G to generate a second current i2. The ring oscillator 64 is electrically connected to the second current mirror 62 and the frequency divider 50 and receives the second current i2 to generate the alternating current oscillating signal O. Since the sources of the first NMOSFET 54 and the third NMOSFET 58 are electrically connected to each other, process variations have a reduced influence on the frequency of the alternating current oscillating signal O. Besides, considering area and power, the ring oscillator 64 is a better choice.

In conclusion, the present invention uses the PLL-based phase shift keying demodulator to precisely and rapidly obtain digital data when the binary data change.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. An implantable wireless device for transmitting data comprising:
    an external control device comprising:
        a phase shift keying (PSK) modulator receiving digital data and an alternating current (AC) carrier signal and using the AC carrier signal to modulate the digital data into a phase shift keying (PSK) modulation signal, and the digital data have a plurality of time points that binary data change; and
        a first wireless transmission coil whose quality factor is larger than 100, and the first wireless transmission coil is electrically connected to the phase shift keying modulator; and
    an internal processing device implanted in a physiological tissue and comprising:
        a second wireless transmission coil whose quality factor is larger than 100;

a phase-lock loop (PLL)-based phase shift keying demodulator electrically connected to the second wireless transmission coil, receiving the phase shift keying modulation signal through the first wireless transmission coil and the second wireless transmission coil, and obtaining a ripple voltage signal according to the phase shift keying modulation signal, and the ripple voltage signal decreases from a fixed voltage value at each of the plurality of time points and then increases to the fixed voltage value, and the phase-lock loop-based phase shift keying demodulator demodulates the ripple voltage signal into the digital data; and an alternating current (AC) to direct current (DC) converter electrically connected to the second wireless transmission coil, receiving the phase shift keying modulation signal through the first wireless transmission coil and the second wireless transmission coil, and converting the phase shift keying modulation signal into a supplying direct current voltage.

2. The implantable wireless device for transmitting data according to claim 1, wherein the phase-lock loop-based phase shift keying demodulator further comprises:

a phase-lock loop electrically connected to the second wireless transmission coil, receiving the phase shift keying modulation signal through the first wireless transmission coil and the second wireless transmission coil, and obtaining the ripple voltage signal according to the phase shift keying modulation signal;

a triggering detector electrically connected to the phase-lock loop and receiving the ripple voltage signal, and generating a positive pulse signal at each of the plurality of time points; and a logic assembly electrically connected to the triggering detector to receive the positive pulse signal, thereby generating the digital data.

3. The implantable wireless device for transmitting data according to claim 2, wherein the triggering detector further comprises:

a low pass filter electrically connected to the phase-lock loop and receiving the ripple voltage signal to generate a filtering signal;

a comparator having a positive input terminal, a negative input terminal, and an output terminal, the negative input terminal of the comparator is electrically connected to the phase-lock loop and the low pass filter, the low pass filter is electrically connected between the positive input terminal and the negative input terminal of the comparator, the positive input terminal and the negative input terminal of the comparator respectively receive the filtering signal and the ripple voltage signal, and the comparator compares the filtering signal with the ripple voltage signal and uses the output terminal to generate a comparison signal; and a Schmitt trigger electrically connected to the output terminal of the comparator and the logic assembly to receive the comparison signal and generate the positive pulse signal at each of the plurality of time points according to the comparison signal.

4. The implantable wireless device for transmitting data according to claim 2, wherein the logic assembly is a DQ flip-flop.

5. The implantable wireless device for transmitting data according to claim 2, wherein the phase-lock loop-based phase shift keying demodulator further comprises a clock recovery circuit electrically connected to the second wireless transmission coil and the triggering detector, receiving the positive pulse signal and the phase shift keying modulation signal, and dividing a frequency of the phase shift keying modulation signal by a given value to generate a clock signal, a frequency of the clock signal corresponds to a data rate of the digital rate, and when the clock recovery circuit receives the positive pulse signal, the clock recovery circuit resets the clock signal.

6. The implantable wireless device for transmitting data according to claim 5, wherein a period of the clock signal is A seconds, the data rate is B bits per second, A is a positive number, B is a natural number, and A×B=1.

7. The implantable wireless device for transmitting data according to claim 6, wherein the internal processing device further comprises a processor electrically connected to the logic assembly and the clock recovery circuit and receiving the clock signal and the digital data, and when the clock signal rises from a negative level to a positive level, the processor retrieves the digital data.

8. The implantable wireless device for transmitting data according to claim 2, wherein the phase-lock loop further comprises:

a phase frequency detector electrically connected to the second wireless transmission coil, receiving the phase shift keying modulation signal through the first wireless transmission coil and the second wireless transmission coil, receiving an alternating current feedback signal, and using the alternating current feedback signal and the phase shift keying modulation signal to generate a first digital value and a second digital value;

a charge pump circuit electrically connected to the phase frequency detector and receiving the first digital value and the second digital value;

a loop filter electrically connected to the charge pump circuit and the triggering detector, the charge pump circuit uses a current source to charge or discharge the loop filter according to the first digital value and the second digital value, so as to transmit a current signal to the loop filter, and the loop filter converts the current signal into the ripple voltage signal;

a voltage controlled oscillator electrically connected to the loop filter and receiving the ripple voltage signal to generate an alternating current oscillating signal; and a frequency divider electrically connected to the voltage controlled oscillator and the phase frequency detector, receiving the alternating current oscillating signal, and dividing a frequency of the alternating current oscillating signal by a fixed value to generate the alternating current feedback signal.

9. The implantable wireless device for transmitting data according to claim 8, wherein the voltage controlled oscillator further comprises:

a first current mirror generating a first current;

a first N-channel metal oxide semiconductor field effect transistor (NMOSFET) with a drain thereof electrically connected to the first mirror and a gate of the first NMOSFET is electrically connected to the loop filter and the triggering detector to receive the ripple voltage signal;

a second N-channel metal oxide semiconductor field effect transistor (NMOSFET) with a drain thereof electrically connected to a source of the first NMOSFET, and a gate of the second NMOSFET is electrically connected to the drain of the first NMOSFET, and a source of the second NMOSFET is grounded, and the first NMOSFET and the second NMOSFET uses the ripple voltage signal to receive the first current, thereby establishing a node voltage at the source of the first NMOSFET;

a third N-channel metal oxide semiconductor field effect transistor (NMOSFET) with a source thereof electrically connected to the source of the first NMOSFET and the drain of the second NMOSFET to receive the node voltage, and a gate of the third NMOSFET receives a high level voltage;

a controller electrically connected to a drain of the third NMOSFET, receiving an external voltage, and using the external voltage to turn on the third NMOSFET and generate a start voltage;

a second current mirror electrically connected to the controller and receiving the start voltage to generate a second current; and a ring oscillator electrically connected to the second current mirror and the frequency divider and receiving the second current to generate the alternating current oscillating signal.

10. The implantable wireless device for transmitting data according to claim 1, wherein the phase shift keying modulator is a binary phase shift keying (BPSK) modulator, the phase shift keying modulation signal is a binary phase shift keying modulation signal, and the phase-lock loop-based phase shift keying demodulator is a phase-lock loop-based binary phase shift keying demodulator.

* * * * *